US00PP24487P2

(12) United States Plant Patent
Robb

(10) Patent No.: US PP24,487 P2
(45) Date of Patent: May 20, 2014

(54) *SCABIOSA* PLANT NAMED 'SGIPU2-0'

(50) Latin Name: *Scabiosa columbaria*
Varietal Denomination: SGIPU2-0

(75) Inventor: John Robb, Kulnura (AU)

(73) Assignee: The Paradise Seed Company Pty. Ltd. (AU)

( * ) Notice: Subject to any disclaimer, the term of this patent is extended or adjusted under 35 U.S.C. 154(b) by 0 days.

(21) Appl. No.: 13/506,790

(22) Filed: May 16, 2012

(51) Int. Cl.
*A01H 5/00* (2006.01)

(52) U.S. Cl.
USPC ..... Plt./478

(58) Field of Classification Search
USPC ..... Plt./478
See application file for complete search history.

*Primary Examiner* — Annette Para
(74) *Attorney, Agent, or Firm* — Cassandra Bright

(57) ABSTRACT

A new and distinct *Scabiosa* cultivar named 'SGIPU2-0' is disclosed, characterized by large, purple-violet colored flowers and unique thick flower stems. The new variety is a *Scabiosa*, suitable as an outdoor garden or container plant.

2 Drawing Sheets

Figure 1:
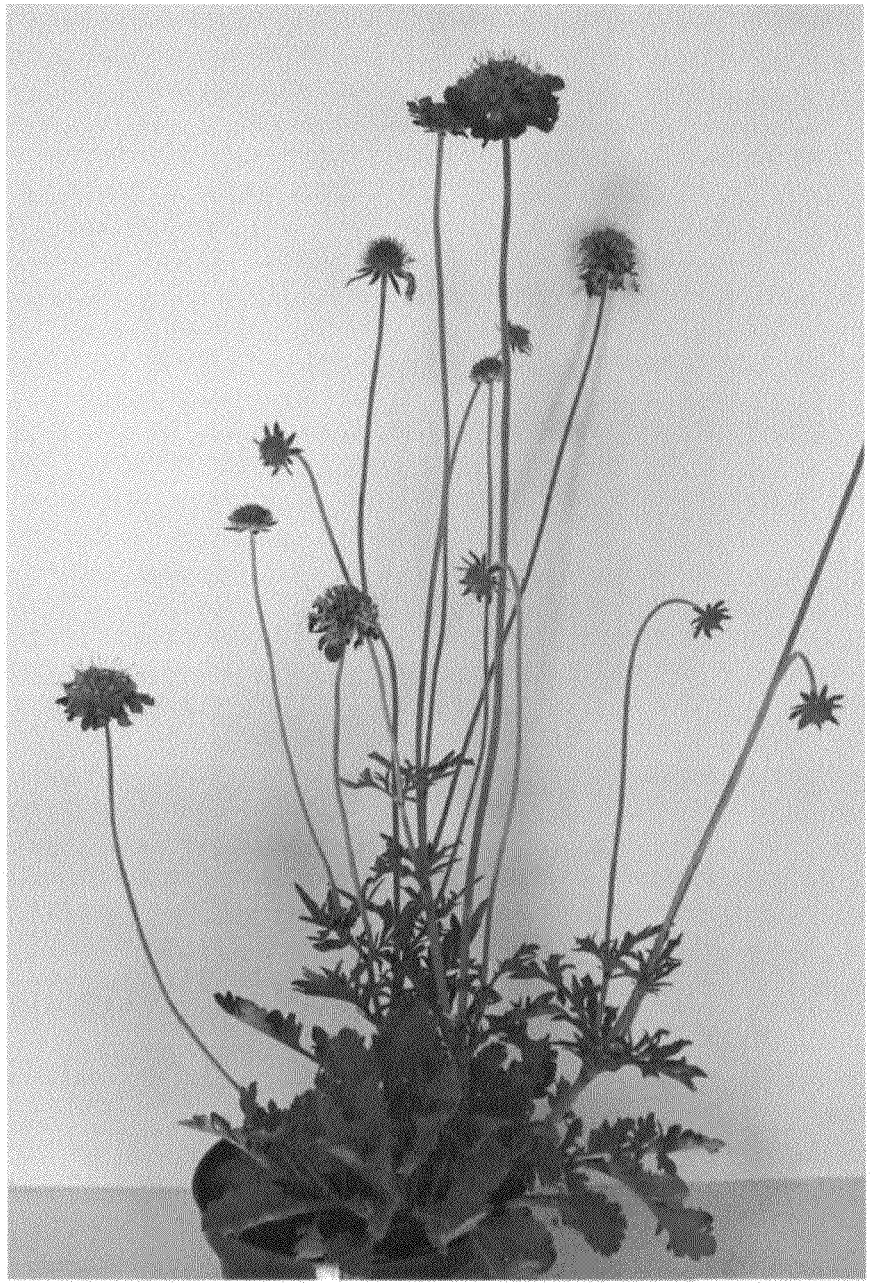

Latin name of the genus and species: *Scabiosa columbaria.*
Variety denomination: 'SGIPU2-0'.

The new *Scabiosa* cultivar is the product of a planned breeding program by the inventor John Robb, a citizen of Australia. The breeding program was carried out in Kulnura, New South Wales, Australia. The objective of the breeding program was to develop new *Scabiosa* varieties with good characteristics for ornamental purposes.

The new variety resulted from the crossing of the seed parent, an unnamed, unpatented proprietary *Scabiosa* seedling with the pollen parent, an unnamed, unpatented proprietary *Scabiosa* seedling on February 1 of 2002. The new variety was discovered on February 13 of 2003 by the inventor in a group of seedlings resulting from the 2002 crossing, in a commercial greenhouse in Kulnura, New South Wales, Australia.

Asexual reproduction of the new cultivar 'SGIPU2-0' by vegetative cuttings was first performed at a commercial greenhouse in Kulnura, New South Wales, Australia on February 15 of 2003. Subsequently at least five generations have been produced from vegetative cuttings, and have shown that the unique features of this cultivar are stable and reproduced true to type. After observing the new variety confidentially over multiple seasons, the variety was also propagated in tissue culture, in a controlled laboratory, without access by third parties.

SUMMARY OF THE INVENTION

The cultivar 'SGIPU2-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SGIPU2-0.' These characteristics in combination distinguish 'SGIPU2-0' as a new and distinct *Scabiosa* cultivar:

1. Purple-Violet colored flowers.
2. Distinctive thick flowering stem.
3. Large flower size.

COMPARISON TO THE PARENT VARIETIES

Plants of the new cultivar 'SGIPU2-0' are similar in most horticultural characteristics to plants of the unnamed, unpatented proprietary seed parent. However, the new variety has a larger overall flower size and thicker flower stem than the seed parent. Also the plant is taller than the seed parent. Additionally, 'SGIPU2-0' produce a darker colored flower than the seed parent.

Plants of the new cultivar 'SGIPU2-0' are similar in most horticultural characteristics to plants of the unnamed, unpatented proprietary pollen parent. However, the new variety has a larger overall flower size and thicker flower stem than the pollen parent. Also the plant is taller than the pollen parent. Additionally, plants of 'SGIPU2-0' produce a much darker colored flower than the pollen parent.

COMPARISON TO COMMERCIAL VARIETY

The new cultivar can be compared to the commercial variety 'SGIBL01-0', U.S. plant patent application Ser. No. 13/385,907, currently pending before the USPTO. Plants of the two cultivars are similar in most horticultural characteristics, however, plants of 'SGIPU2-0' produce a darker colored flower, with stronger purple coloration.

BRIEF DESCRIPTION OF THE PHOTOGRAPHS

The accompanying photograph in FIG. 1 illustrates in full color a typical flower of 'SGIPU2-0'.

Figure 2:
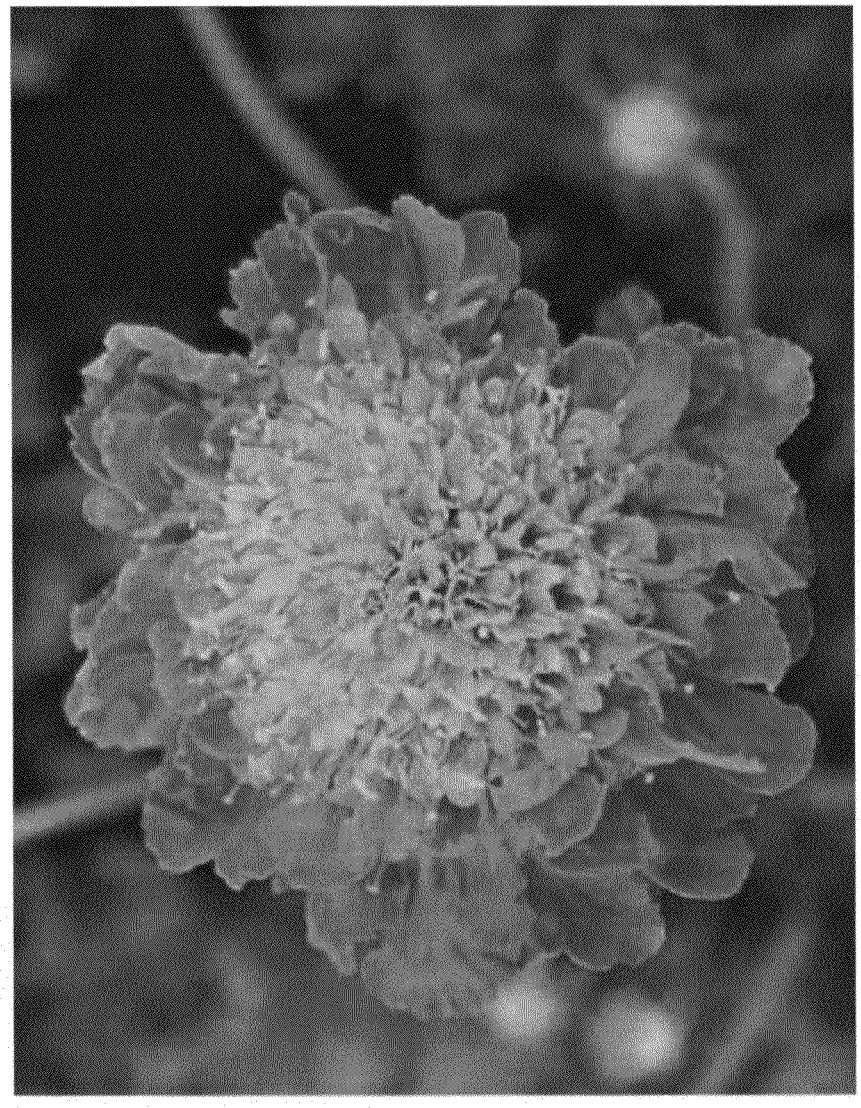

FIG. 2 illustrates a typical plant of 'SGIPU2-0' grown in a greenhouse, in a 6 inch commercial pot. Age of the plant photographed is approximately 30 weeks from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurement describe 'SGIPU2-0' plants grown in a commercial greenhouse in Oxnard, Calif. The growing temperature ranged from approximately 12° C. to 30° C. The greenhouse is subject to partial shade. General light conditions are bright, normal sunlight with some shade during the brightest part of the day. Measurements and numerical values represent averages of typical plant types.

Botanical classification: *Scabiosa columbaria* 'SGIPU2-0'.

PROPAGATION

Time to initiate roots: About 10 to 15 days at approximately 20 to 25° C.

Root description: Fine, fibrous.

PLANT

Growth habit: Upright.

Age of the plant described: Approximately 20 weeks from a well rooted cutting.

Pot size of plant described: 6 inch pot.

Height: Approximately 21 cm from soil line to top of foliar plane. Approximately 48 cm to top of highest flower.

Plant spread: Approximately 25 cm at widest point.

Growth rate: Moderate.

Branching characteristics: Basal rosettes of main stems with smaller lateral branches.

Length of primary stems: Approximately 17 cm.

Quantity of primary lateral branches: Average 5.

Characteristics of primary lateral branches:

*Diameter*.—Approximately 0.7 cm.

*Color*.—Near RHS Green 143C.

*Texture*.—Highly pubescent, soft, dense, velvety.

*Strength*.—Very strong.

Internode length: Average range to 10 cm.

FOLIAGE

Leaf:

*Arrangement*.—Opposite.

*Quantity*.—Basal rosettes with average 12 leaves.

*Average length*.—Approximately 16.5 cm.

*Average width*.—Approximately 5.0 cm.

*Shape of blade*.—Overall shape obovate, pinnatifid.

*Apex*.—Acute.

*Base*.—Attenuate.

*Margin*.—Dentate.

*Appearance of top surface*.—Matte.

*Appearance of top surface*.—Matte.

*Pubescence*.—Very short, soft, less than 1 mm hairs, densely covering top and bottom leaf surfaces.

*Aspect*.—Very slightly undulating, overall leaf, including petiole, reflexes downward. Leaf blade slightly folds up from the mid vein.

*Color*.—Young foliage upper side: Near RHS Green 137C. Young foliage under side: Near RHS Green 137C. Mature foliage upper side: Near RHS Green 137A. Mature foliage under side: Near RHS Green 137C.

*Venation*.—Type: Pinnate. Venation color upper side: Near RHS Green 143C. Venation color under side: Near RHS Green 143C.

*Petiole*.—Length: Average range between 2.5cm to 6.0 cm. Diameter: Approximately 0.5 cm. Color: Near RHS Yellow-Green 145B. Texture: Pubescent.

FLOWER

Natural flowering season: Spring and Summer.

Time to flowering from rooted cutting: Approximately 15 weeks.

Inflorescence and flower type and habit: Terminal composite inflorescence, round, with numerous complete flowers. Outer flowers larger than the inner flowers. Approximately 30 large and 60 smaller flowers per inflorescence.

Rate of flower opening: Approximately 2 weeks from bud to fully opened flower.

Inflorescence longevity on plant: At least 2 weeks before any significant change is observed. Individual flowers become dry, without significant color change.

Approximate quantity of flowers per plant: Approximately 15 mature and immature inflorescence per plant.

Flowers persistent:

Inflorescence:

*Diameter of entire inflorescence*.—Approximately 6.0 cm.

*Depth of inflorescence*.—Approximately 3.1 cm.

*Inner cushion diameter*.—Approximately 3.0 cm.

*Receptacle shape*.—Dome.

*Receptacle height*.—Average 0.7 cm.

*Receptacle diameter*.—Average 1.2 cm.

*Receptacle color*.—Near RHS Yellow-Green 144D.

Individual flower bud:

*Shape*.—Sphere.

*Length*.—Approximately 0.3 cm.

*Diameter*.—Approximately 0.2 cm.

*Color*.—Near RHS Green 143C.

Large outer flowers:

*Flower length:* 2.5 cm.

*Flower width:* 2.0 cm.

*Upper petals* (*upper lip*).—Number: 4, fused together at base. Length: 0.5 cm. Width: 0.5 cm. Shape: Obicular. Margin: Entire. Texture: Glabrous, matte. Color: When opening: Upper surface: RHS Violet 83D. Lower surface: RHS Violet 83D. Fully opened: Upper surface:. RHS Purple-Violet N82B. Lower surface: RHS Purple-Violet N82B.

*Lower petals* (*lower lip*).—Quantity: 3. Length: 1.8 cm. Width: 1.0 cm. Shape: Spatulate, all 3 petals fused together at base. Apex shape: Obtuse, with minutely shallow lobes. Ruffled appearance. Color: When opening: Upper surface: RHS Purple-Violet N82A, but darker. Lower surface: RHS Purple-Violet N82B with center blotch near N82D. Fully opened: Upper surface: RHS Purple-Violet N82A, flush Purple-Violet N81A on center of petal, margins Violet 83A. Lower surface: RHS Purple-Violet N82D, margins Violet 83A.

*Throat*.—Length: 0.6 cm. Width: 0.15 cm. Texture: glabrous, shiny. Color: Near Violet 84D, inner and outer surfaces.

*Bracteole*.—Quantity: 6 per flower. Length: Average 0.6 cm. Diameter: less than 0.1 cm. Shape: Linear. Texture: Glabrous, shiny. Color: Near RHS Purple 79A.

Smaller inner flowers:

*Flower length*.—1.3 cm.

*Flower width*.—0.8 cm.

*Upper petals* (*upper lip*).—Number: 2, fused together at base. Length: 0.3 cm. Width: 0.3 cm. Shape: Obicular. Margin: Entire or ruffled. Texture: Glabrous, matte. Color: When opening: Upper surface: RHS Purple-Violet N82D. Lower surface: RHS Purple-Violet N82D. Fully opened: Upper surface: RHS Purple-Violet N82C. Lower surface: RHS Purple-Violet N82D.

*Lower petals* (*lower lip*).—Quantity: 3. Length: 0.4 cm. Width: 0.3 cm. Shape: Spatulate. Apex shape: Obtuse, with minutely shallow lobes. When opening: Color: When opening: Upper surface: RHS Purple-Violet N82C. Lower surface: RHS Purple-Violet N82D. Fully opened: Upper surface: RHS Purple-Violet N82C, margin N82A. Lower surface: RHS Purple-Violet N82D.

*Throat*.—Length: 0.4 cm. Width: 0.2 cm. Texture: glabrous, shiny. Color: Near Purple 76D, inner and outer surfaces.

*Bracteole*.—Quantity: 6 per flower. Length: Average 0.6 cm. Diameter: less than 0.1 cm. Shape: Linear, hair-like. Texture: Glabrous, shiny. Color: Near RHS Purple N79A.

Flower color fading: No noticeable color change observed.

Phyllaries/involucral bracts:

*Quantity per inflorescence*.—Average 12.

*Shape*.—Oblanceolate.

*Length*.—Approximately 0.8 cm.

*Width*.—Approximately 0.2 cm.

*Apex*.—Acute.

*Base*.—Truncate.

*Margin*.—Entire.

*Texture*.—Pubescent, all surfaces.

*Color*.—Upper Surface: Near RHS Green 137A. Lower Surface: Near RHS Green 137A.

Peduncle:

*Length*.—Longest average 33 cm. Shortest average 20 cm.

*Diameter*.—Approximately 0.6 cm.

*Texture*.—Densely pubescent. Hairs moderately stiff, appressed.

*Color*.—Near RHS Green 138A.

*Orientation*.—Approximately 30 degree angle from stem. Moderate undulation.

Fragrance: Faint, slightly sweet.

REPRODUCTIVE ORGANS

Reproductive organs identical in both size flowers.

Stamens:

*Number*.—4.

*Filament length*.—Approximately 0.5 cm.

Anthers:

*Length*.—Approximately 0.1 cm.

*Shape*.—Linear.

*Color*.—Near RHS Red-Purple 69D.

*Pollen*.—Not observed.

Pistil:

*Number*.—1.

*Length*.—Approximately 1.2 cm.

*Style*.—Length: Approximately 1.1 cm. Color: Near RHS Red-Purple 69D.

*Stigma*.—Shape: Oblate. Color: Near RHS Purple N79C.

OTHER CHARACTERISTICS

Seeds and fruits: Not observed.

Disease/pest resistance: Neither resistant nor susceptible to normal diseases and pests of *Scabiosa*.

Temperature tolerance: USDA zones 3-9.

What is claimed is:

1. A new and distinct cultivar of *Scabiosa* plant named 'SGIPU2-0' as herein illustrated and described.

* * * * *